(12) United States Patent
Ondrus et al.

(10) Patent No.: US 6,751,581 B1
(45) Date of Patent: Jun. 15, 2004

(54) METHOD FOR SIMULATING THE FORMATION OF AN ADHESIVE JOINT

(75) Inventors: Daniel Joseph Ondrus, Northville, MI (US); Keith David Thompson, Ann Arbor, MI (US)

(73) Assignee: Ford Motor Company, Dearborn, MI (US)

( * ) Notice: Subject to any disclaimer, the term of this patent is extended or adjusted under 35 U.S.C. 154(b) by 0 days.

(21) Appl. No.: 09/569,205

(22) Filed: May 11, 2000

(51) Int. Cl.$^7$ ................................................. G06G 7/48
(52) U.S. Cl. ................................. 703/6; 703/12; 702/41
(58) Field of Search .......................... 703/6, 12; 702/41; 156/60, 274.8; 427/472

(56) References Cited

U.S. PATENT DOCUMENTS

| | | | |
|---|---|---|---|
| 4,759,489 A | 7/1988 | Pigott | 228/102 |
| 5,277,737 A * | 1/1994 | Li et al. | 156/274.8 |
| 5,362,120 A | 11/1994 | Cornille, Jr. | 296/203 |
| 5,849,122 A | 12/1998 | Kenmochi et al. | 156/182 |
| 6,127,002 A * | 10/2000 | Callahan, Jr. et al. | 427/472 |
| 6,233,896 B1 * | 5/2001 | Coup | 52/586.1 |
| 6,539,314 B1 * | 3/2003 | Ondrus et al. | 702/41 |
| 2003/0075256 A1 * | 4/2003 | Ondrus | 156/60 |

OTHER PUBLICATIONS

Dorn, L., "Adhesive Joints—Design and Calculation", Technische Universitat, Berlin, 1994.*
Loctite, "Design considerations for an adhesive joint", Loctite Worldwide design handbook, section 9.3, 1996–1997.*
Sevigny, R., "Cost-effective adhesive assemblies", Appliance manufacturer, Jul. 1999.*
Gabrielson, "Designing for assembly with adhesive", Design News, Jan. 2000.*

\* cited by examiner

Primary Examiner—Kevin J. Teska
Assistant Examiner—Kandasamy Thangavelu
(74) Attorney, Agent, or Firm—David B. Kelley

(57) ABSTRACT

A method for simulating the formation of an adhesive joint and/or for determining the attributes of the adhesive joint is disclosed. The method allows an individual or business enterprise to consistently and reliably determine a proper amount and placement of adhesive used to form the joint.

28 Claims, 2 Drawing Sheets

US 6,751,581 B1

METHOD FOR SIMULATING THE FORMATION OF AN ADHESIVE JOINT

FIELD OF INVENTION

The present invention relates to a method for simulating the formation of an adhesive joint. More specifically, the present invention relates to a method for simulating the formation of an adhesive joint which allows the proper size and location of an adhesive bead, which is to form an adhesive joint, to be accurately determined and/or allows attributes of an adhesive joint to be accurately determined given a size and location of an adhesive bead used to form the joint.

BACKGROUND OF THE INVENTION

Adhesive joints (e.g., joints formed of glues, polymers and/or other adhesives) are often utilized to connect and/or attach components of articles of manufacture. Such joints are typically formed by placing an amount of adhesive (i.e., a generally spherical bead) in a particular position or at a particular location on a first component and then moving the first component and a second component together, thereby compressing the adhesive between the first and second components to form a joint.

It is desirable to develop methods which determine the appropriate amount and/or placement of adhesive on a component such that the adhesive forms a durable joint. An appropriate amount and/or placement of adhesive, as used herein, refers to an amount large enough to form a joint of adequate strength, but small enough and appropriately placed such that excess adhesive is not "squeezed" or discharged from between the first and second components, thereby wasting adhesive and/or interfering with other components of the article of manufacture.

A conventional method for determining the amount and/or placement of adhesive which is to form a joint typically includes "trial and error" type processes. That is, an amount of adhesive is typically placed in a particular position on a first component and a joint is formed with a second component. If the joint produces wasted or excessive discharged adhesive, a lesser amount of adhesive or a different placement of the adhesive is used to form a new joint. If the joint is too weak, additional adhesive is used to form another joint. This process may be repeated to form additional joints using more or less adhesive placed in different locations on the components until an adequate or desirable joint is formed. This conventional trial and error method suffers from drawbacks. In particular, the conventional method undesirably requires excessive cost and time for experimentation and may consume several samples or prototypes before a proper joint is produced.

Therefore, it is desirable to provide a method for simulating an adhesive joint which allows an individual and/or business enterprise to form consistent and reliable joints with minimal experimentation.

SUMMARY OF THE INVENTION

It is a first object of the present invention to provide a method for simulating the formation of an adhesive joint which overcomes the previously delineated drawbacks of conventional methods.

It is a second object of the present invention to provide a method for simulating the formation of an adhesive joint which allows an adequate joint to be consistently formed with minimal experimentation.

According to a first aspect of the present invention, a method is provided for simulating the formation of an adhesive joint which attaches components of an article of manufacture. The method includes the steps of determining first variables of the components which effect the formation of the joint; determining second variables relating to an adhesive bead used to form the joint; formulating at least one equation which interrelates the first and the second variables; and utilizing the at least one equation to simulate the formation of the adhesive joint.

These and other objects, aspects, and advantages of the present invention will become apparent upon reading the following detailed description in combination with the accompanying drawings.

DETAILED DESCRIPTION OF THE PREFERRED EMBODIMENT OF THE INVENTION

Figure 1:
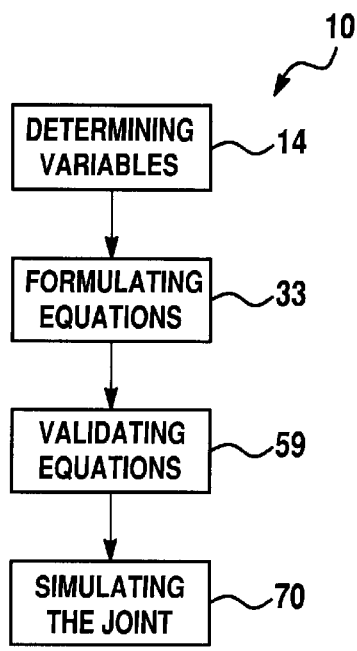
FIG. 1 illustrates a flowchart of a method for simulating the formation of an adhesive joint according to a preferred embodiment of the present invention.

Referring now to FIG. 1, there is shown a flowchart or flow diagram illustrating a method 10 for simulating the formation of an adhesive joint which allows a business enterprise to consistently and accurately determine the size and/or amount of adhesive and the location of the adhesive that is required to form an adequate adhesive joint. Method 10 is further effective to determine attributes of a particular joint given the size or amount of adhesive and the location of the adhesive used to form the joint. The adhesive joints discussed herein, connect or attach two components of an article of manufacture. While the joint 30 described herein and shown in FIG. 2(c) is a "full coach" joint, it should be appreciated that the method 10 can be used to simulate other types of joints such as a half coach or a lap joint.

The method 10 begins with a step 14 of determining and/or selecting variables which will effect the formation of the joint. In one non-limiting embodiment of the invention, the variables which effect the formation of the joint include, but are not limited to attributes of the joint itself (e.g., joint type or thickness), and attributes of (e.g., the geometry of) the components which are connected by the adhesive when the joint is formed. These "geometric" variables at least partially define the shape of the joint. Other variables which may be determined include variables related to the attributes of the adhesive used to form the joint (e.g., the sectional area/diameter of adhesive bead used to form the joint and the location or placement of the adhesive which is used to form the joint), and other conditions such as heat (i.e., temperature) and humidity.

Figure 2A:
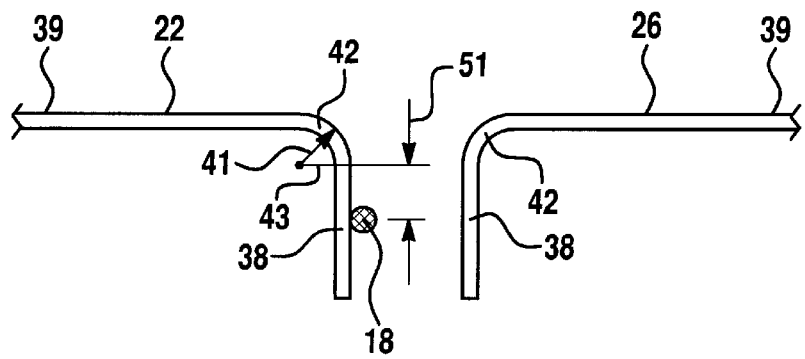
FIG. 2(a) illustrates a first sectional view of a first and second component which are to be connected by an adhesive joint.
Figure 2B:
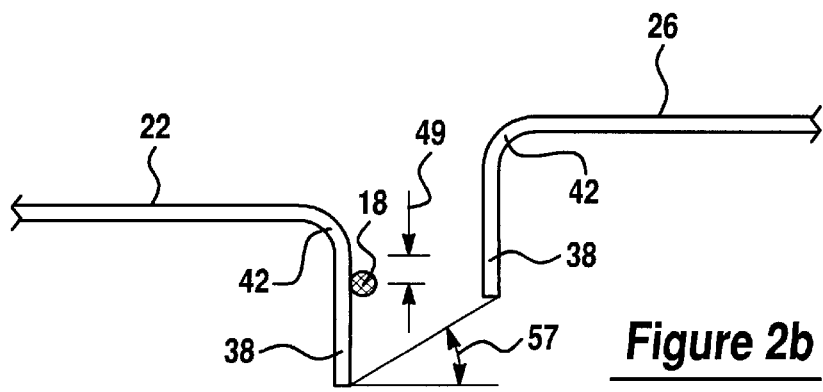
FIG. 2(b) illustrates a second sectional view of a first and second component which are to be connected by an adhesive joint.
Figure 2C:
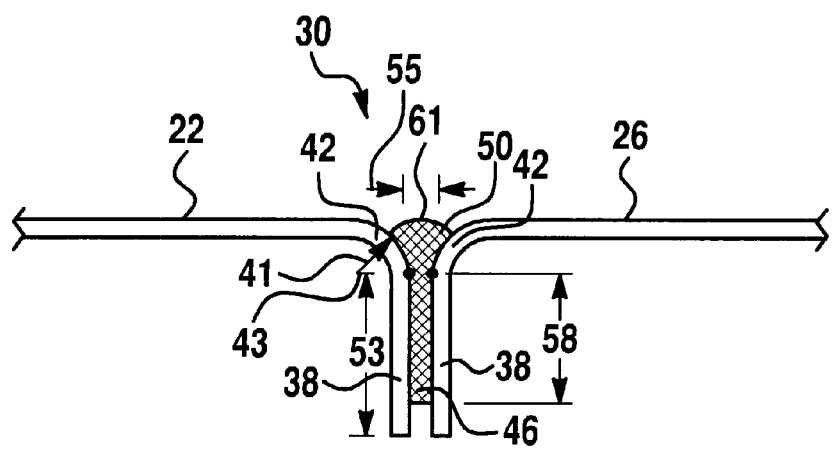
FIG. 2(c) illustrates a sectional view of the first and second components of FIGS. 2(a) and 2(b) after the components have been connected to form a full coach adhesive joint.

In the preferred embodiment and referring to FIGS. 2(a), 2(b) and 2(c), variables are determined and/or selected which effect the formation of adhesive joint 30. Joint 30 is formed by placing an adhesive bead 18 on a first component 22 of an article of manufacture, and then moving the first component 22 and a second component 26 together such that the bead 18 is compressed or "squeezed" to form the joint 30 which connects the first and second components 22, 26. In the preferred embodiment of method 10, the components 22, 26 are connected by the adhesive joint 30 to form a full coach joint 30, as shown in FIG. 2(c). Components 22, 26 each respectively include a "joint contacting" or flange portion 38, an arcuate portion 42, and a generally elongated portion 39.

The preferred embodiment, variables may be selected or determined using engineering judgment, knowledge, physical laws and properties, previous experience, or in any other suitable manner. In one non-limiting embodiment, the following variables are determined/selected as the variables which effect the formation of joint 30:

Bending Radius (R) is the radius of curvature 41 of arcuate portions 42 of the components 22, 26. Bending radius is determined as a variable, since the arcuate portions 42 at least partially define the geometry of fillet 50. The value for the bending radius is obtained in a conventional manner by measuring the radius 41 of arcuate portions 42.

Adhesive Bead Location is the distance 51 from a line 43 relative to the bending radius where the arcuate portion ends, to the center of the bead 18. Adhesive bead location is determined as a variable because the location of the bead 18 prior to forming the joint 30 at least partially determines the manner in which the adhesive bead will be compressed, thereby at least partially defining the geometry of the joint 30. The adhesive bead location is obtained by measuring the distance from the line 43 of the bending radius to the center of the bead 18 in a conventional manner.

Flange width (W) is the distance 53 between the edge of the flange portion 38 and the line 43 at the bend radius.

Flange width at least partially defines the geometry of joint 30 and is obtained by measuring the distance 53 between the edge of the flange portion 38 and the line 43 where the bend radius begins.

Joint Thickness (T) is the final thickness 55 of the joint between the flange portions 38. Joint thickness 55 is determined as a variable, since the joint thickness at least partially defines the sectional area of joint 30. Joint thickness is obtained by measuring the final thickness of the portion of the joint 30 between flange portions 38.

Mating Angle (MA) is the angle 57 at which the flange portions 38 are "brought together" or joined. The mating angle at least partially defines the geometry of the joint 30 and is obtained by conventionally measuring the angle at which the members 22, 26 are "brought together" or joined. In a non-limiting embodiment, mating angle is used to calculate an effective bead location which may be derived by experimental procedures which are designed to relate a joint formed with a zero mating angle to a joint formed with a non-zero mating angle. For example, the bead location shown in FIG. 2(a) (i.e., length 51) may be equivalent to the effective bead location shown in FIG. 2(b) even though the actual bead location (i.e., length 49) shown in FIG. 2(b) is less than length 51, due to the mating angle 57 of joint 32.

Figure 3:
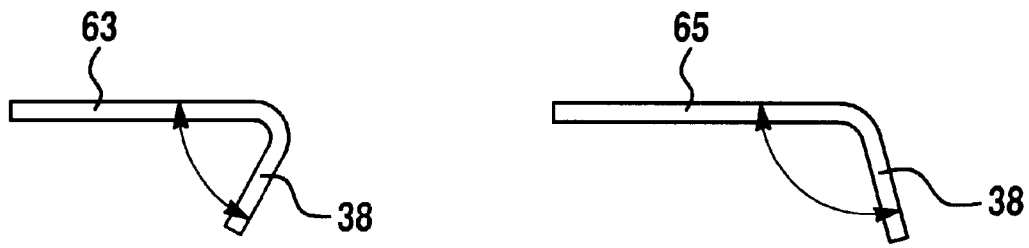
FIG. 3 illustrates a sectional view of other components which may be selectively connected to form an adhesive joint according to the method of the preferred embodiment of the present invention.

Flange Alignment Angle ($\theta$) is the angle between flange portions 38. Flange angle is determined due to its effect on the geometry or shape of joint 30 and/or the direction which the adhesive expands to form joint 30. The variable $\theta$ is measured in a conventional manner as the number of degrees the angles of flanges 38 deviate from 90°. The flange alignment angle for the joint formed by components 22, 26 is zero, because flange portions 38 are both at 90° with respect to portions 39. However, the flange angles for joints formed by other components, such as the components 63, 65 shown in FIG. 3, may be greater than zero (e.g. component 65) or less than zero (e.g. component 63).

Joint Type (A) is the type of joint that is to be formed. Joint type is determined as a variable because it effects the shape of the joint 30. For the preferred embodiment, joint type A may be either full coach or half-coach and respectively equals either one or two. For a lap joint, joint type A is equal to one and radius R is equal to zero.

Adhesive Fillet ($F_F$) represents the proportion of the region between the arcuate portions 42 which contains adhesive from joint 30. $F_F$ is calculated by dividing the sectional area of the fillet 50 by the sectional area or space between portions 42. $F_F$ is a value between zero and one (i.e., $0<F_F<1$).

Flange Coverage ($F_J$) is the proportion of the flange portions 38 covered by adhesive after the joint 30 is formed. $F_J$ is calculated by dividing the length 58 of the flange portions 38 covered with adhesive by the full length 53 of the flange portions 38. $F_J$ is a value for the proportion of flange coverage, ($0<F_J<1$). In one non-limiting embodiment, $F_J$ is a function of the adhesive bead location or the effective bead location.

In step 33, which follows step 10, one or more equations are formulated which interrelate the variables that effect the formation of the joint. In one non-limiting embodiment, the equations that are formulated equate the sectional area of the adhesive bead prior to forming the joint to the sectional area of the joint once it is formed.

In the preferred embodiment, the equations are formulated by use of a first assumption that the adhesive material which is used to form joint 30 is essentially "incompressible", (i.e., the sectional area of the bead that forms joint 30 is equivalent to the sectional area of the joint 30 when the joint is formed). A second assumption is made that a meniscus portion 61 of joint 30 represents a negligible amount of sectional area of the joint 30. Furthermore, a third assumption is made that the adhesive will flow equally in both directions and will be of sufficient viscosity to substantially negate gravitational effects. Based upon these assumptions, in the preferred embodiment of the invention, the sectional area of the adhesive bead 18 is equated to the sectional area of joint 30 according to the following equation:

$$TF_J W + TF_F R + AR^2 \left[ F_F - \frac{\sin^{-1} F_F}{2} - \frac{F_F}{2}\sqrt{1-F_F^2} \right] + B = \frac{\pi D^2}{4} \quad \text{(Eq. 1)}$$

where the left side of the equation is the sectional area of the joint 30 and the right side of the equation is the sectional area of bead 18, and where D represents the diameter of the bead 18, and B equals zero for an alignment angle $\theta$ equal to zero. If the flange alignment angle does not equal zero then B is calculated by use of one of the following equations:

$$B = A \tan\theta \left[ F_f RW + \frac{W^2}{2}(2F_J - F_J^2) \right] \quad \text{(Eq. 2)}$$

for an "underbent" flange (e.g., flange 63), or $$B = \frac{A}{2}\tan\theta \; F_J^2 W^2 \qquad \text{(Eq. 3)}$$

for an "overbent" flange (e.g., flange 65).

In step 59, the equations provided by step 33 are validated or tested. In one non-limiting embodiment, experimental procedures are used to test the accuracy of the equations. For example and without limitation, joints may be formed in differing manners to ensure that the interrelationship between all of the variables, which is provided by the generated equations, is substantially accurate.

Step 70 of the method 10 includes simulating the joint based upon the formulated equations. That is, a simulation is performed in which certain variables are specified, and Equations 1, 2, and/or 3 are used to determine values for other unspecified variables. In one non-limiting embodiment of the invention, the step 70 of performing the simulation includes inputting the formulated equations (e.g., Eq. 1, 2, and 3), which interrelate the variables of the joint, into a computer system having a conventional computer software package, effective to allow values for the particular variables to be entered into the equations, and to solve for and output values for the unspecified variable(s).

In one non-limiting embodiment, the simulation includes a visual representation that depicts the joint that is being simulated. The visual representation is formed in a conventional manner using computer aided design ("CAD") software and/or any other computer software which can produce a visual representation based on values received by the software. The visual representation shows the joints as formed according to the formulated equations and variables.

In another non-limiting embodiment of the invention, values for the desired joint variables are inputted to the simulation, and the simulation outputs a range or "window" of values for amounts of adhesive and/or locations of adhesive which will produce a desired or adequate joint. In one non-limiting embodiment values for T, $F_J$, W, $F_F$, R, A and/or θ, are inputted to the computer, and the computer produces a range or "window" of appropriate values for B and D which would form an adequate and desirable joint. In other alternate embodiments any other variables may be entered or specified and used to solve for unspecified variables.

It should be recognized that the simulation of an adhesive joint allows an individual to accurately predict the proper amount and/or placement of adhesive to the form a particular joint and/or to predict the shape or size of a joint that will be formed by a particular amount and/or placement of adhesive. The simulation thereby allows an individual to minimize wasteful experiments with actual components of articles of manufacture.

It should be understood that the invention is not limited to the exact embodiment or construction which has been illustrated and described but that various changes may be made without departing from the spirit and the scope of the invention.

What is claimed is:

1. A method for determining an amount and placement of adhesive in simulating the formation of an adhesive joint between a first component and a second component, said method comprising the steps of:

determining at least one first variable relating to attributes of the joint;

determining at least one second variable relating to attributes of the adhesive used to form the joint;

defining an interrelationship between the first and second variable variables by relating a sectional area of the adhesive prior to forming the joint to the sectional area of the joint after forming the joint;

validating the defined interrelationship between the first and second variables; and utilizing the validated interrelationship to simulate the amount of adhesive and placement of adhesive to form the joint.

2. The method of claim 1 further comprising the steps of:

determining at least one third variable relating to attributes of the first and second components which affect the formation of the joint; and defining an interrelationship between the third variable and the first and second variables.

3. The method of claim 1 wherein the first variable is a joint type.

4. The method of claim 3 wherein the first variable is a joint thickness.

5. The method of claim 4 wherein the second variable is a diameter of an adhesive bead.

6. The method of claim 5 wherein the second variable further includes an adhesive bead location on either one of the first component or the second component.

7. The method of claim 6 wherein the third variable includes a flange width of either one of the first component or the second component.

8. The method of claim 7 wherein said step of defining an interrelationship between the first and second variables includes the step of equating the sectional area of the joint to the sectional area of the adhesive, using $$TF_J W + TF_F R + AR^2 \left[ F_F - \frac{\sin^{-1} F_F}{2} - \frac{F_F}{2}\sqrt{1 - F_F^2} \right] + B = \frac{\pi D^2}{4}$$

such that:

D is the diameter of the bead;

$F_J$ is the flange coverage measured as the proportion of the flange portions of either one of the first or second components that is covered by adhesive;

R is the bending radius of curvature of an arcuate portion of either one of the first or second components;

B is the adhesive bead location measured from a line relative to the bending radius where the arcuate portion ends, to the center of the bead;

W is the flange width measured from an edge of a flange portion of either one of the first or second component to the line relative to the bending radius where the arcuate portion ends to the center of the bead;

T is the joint thickness between the flange portions of the first and second components;

θ is the flange alignment angle between the flange portions of the first and second components;

A is the type of joint;

$F_F$ is the adhesive fillet measured as the proportion of the region between the arcuate portions of either one of the first or second components which contains adhesive; and wherein B is zero if θ is zero, or determined using $$B = A\,\tan\theta\left[F_f RW + \frac{W^2}{2}(2F_J - F_J^2)\right]$$

if θ is less than 90° or $$B = \frac{A}{2}\tan\theta\, F_j^2 W^2$$

if θ is greater than 90°.

9. The method of claim 8 further comprising the steps of:
specifying values for variables T, $F_J$, W, $F_F$, R, A and θ;
entering the specified variables into a computer system having a software program for modeling a joint; and
using the computer software joint modeling program to determine the adhesive bead location (B) and bead diameter (D) for the specified variables.

10. The method of claim 9 further including the step of using the computer software joint modeling program to generate a visual representation of the joint.

11. The method of claim 9 wherein the joint is a full coach adhesive joint.

12. The method of claim 9 wherein the joint is a half coach adhesive joint.

13. A method for determining an amount and placement of adhesive in simulating the formation of an adhesive joint between a first component and a second component, said method comprising the steps of:
determining at least one first variable relating to attributes of the joint;
determining at least one second variable relating to attributes of the adhesive used to form the joint;
determining at least one third variable relating to attributes of the first and second components which affect the formation of the joint
defining an interrelationship between the first, second and third variables by relating a sectional area of the adhesive prior to forming the joint to the sectional area of the joint after forming the joint;
validating the defined interrelationship between the first and second and third variables; and
utilizing the validated interrelationship to simulate the amount of adhesive and placement of adhesive to form the joint using a computer software program for modeling a joint.

14. The method of claim 13 wherein the first variable is a joint type.

15. The method of claim 14 wherein the first variable is a joint thickness.

16. The method of claim 15 wherein the second variable is a diameter of an adhesive bead.

17. The method of claim 16 wherein the second variable further is an adhesive bead location on either one of the first component or the second component.

18. The method of claim 12 wherein the third variable is a flange width of either one of the first component or the second component.

19. The method of claim 13 wherein said step of defining an interrelationship between the first, second and third variables includes the step of equating the sectional area of the joint to the sectional area of the adhesive, using $$TF_J W + TF_F R + AR^2\left[F_F - \frac{\sin^{-1} F_F}{2} - \frac{F_F}{2}\sqrt{1 - F_F^2}\right] + B = \frac{\pi D^2}{4}$$

such that:
D is the diameter of the bead;
$F_J$ is the flange coverage measured as the proportion of the flange portions of either one of the first or second components that is covered by adhesive;
R is the bending radius of curvature of an arcuate portion of either one of the first or second components;
B is the adhesive bead location measured from a line relative to the bending radius where the arcuate portion ends to the center of the bead;
W is the flange width measured from an edge of a flange portion of either one of the first or second component to the line relative to the bending radius where the arcuate portion ends, to the center of the bead;
T is the joint thickness between the flange portions of the first and second components;
θ is the flange alignment angle between the flange portions of the first and second components;
A is the type of joint;
$F_F$ is the adhesive fillet measured as the proportion of the region between the arcuate portions of either one of the first or second components which contains adhesive; and
wherein B is zero if θ is zero, or determined using $$B = A\,\tan\theta\left[F_f RW + \frac{W^2}{2}(2F_J - F_J^2)\right]$$

if θ is less than 90° or $$B = \frac{A}{2}\tan\theta\, F_j^2 W^2$$

if θ is greater than 90°.

20. The method of claim 19 further comprising the steps of:
specifying values for variables T, $F_J$, W, $F_F$, R, A and θ;
entering the specified variables into the computer software joint modeling program; and
using the computer software joint modeling program to determine the adhesive bead location (B) and bead diameter (D) for the specified variables.

21. The method of claim 20 further including the step of using the computer software joint modeling program to generate a visual representation of the joint.

22. A method for determining an amount and placement of adhesive in simulating the formation of an adhesive joint between a first component and a second component, said method comprising the steps of:
determining at least one first variable relating to attributes of the joint;
determining at least one second variable relating to attributes of the adhesive used to form the joint;
determining at least one third variable relating to attributes of the first and second components which affect the formation of the joint;
defining an interrelationship between the first, second and third variables by equating a sectional area of the adhesive prior to forming the joint to the sectional area of the joint after forming the joint, using $$TF_J W + TF_F R + AR^2 \left[ F_F - \frac{\sin^{-1} F_F}{2} - \frac{F_F}{2} \sqrt{1 - F_F^2} \right] + B = \frac{\pi D^2}{4}$$

such that:

D is the diameter of the bead;

$F_J$ is the flange coverage measured as the proportion of the flange portions of either one of the first or second components that is covered by adhesive;

R is the bending radius of curvature of an arcuate portion of either one of the first or second components;

B is the adhesive bead location measured from a line relative to the bending radius where the arcuate portion ends, to the center of the bead;

W is the flange width measured from an edge of a flange portion of either one of the first or second component to the line relative to the bending radius where the arcuate portion ends to the center of the bead;

T is the joint thickness between the flange portions of the first and second components;

θ is the flange alignment angle between the flange portions of the first and second components;

A is the type of joint;

$F_F$ is the adhesive fillet measured as the proportion of the region between the arcuate portions of either one of the first or second components which contains adhesive;

wherein B is zero if θ is zero, or determined using $$B = A \tan\theta \left[ F_f RW + \frac{W^2}{2} (2F_J - F_j^2) \right]$$

if θ is less than 90° or $$B = \frac{A}{2} \tan\theta \, F_j^2 W^2$$

if θ is greater than 90°;

specifying values for variables T, $F_J$, W, $F_F$, R, A and θ;

entering the specified variables T, $F_J$, W, $F_F$, R, A and θ into the computer software program for modeling a joint;

using the computer software joint modeling program to determine the adhesive bead location (B) and bead diameter (D) for the joint;

validating the defined interrelationship between the first and second and third variables the adhesion bead location and bead diameter;

utilizing the validated interrelationship to simulate the formation of the joint using the computer software joint modeling program.

23. The method of claim 22 wherein the first variable is a joint type.

24. The method of claim 22 wherein the first variable is a joint thickness.

25. The method of claim 22 wherein the second variable is a diameter of an adhesive bead.

26. The method of claim 25 wherein the second variable is an adhesive bead location on either one of the first component or the second component.

27. The method of claim 22 wherein the third variable is a flange width of either one of the first component or the second component.

28. The method of claim 20 further including the step of using the computer software joint modeling program to generate a visual representation of the joint.

* * * * *